US011490945B2

(12) United States Patent
Kazic et al.

(10) Patent No.: US 11,490,945 B2
(45) Date of Patent: Nov. 8, 2022

(54) MICRO-PULSED LIQUID SPRAY FOR COOLING

(71) Applicant: Fotona d.o.o., Ljubljana (SI)

(72) Inventors: Marko Kazic, Dob pri Domzalah (SI); Nejc Lukac, Ljubljana (SI); Blaz Tasic Muc, Kamnik (SI); Matjaz Lukac, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 0 days.

(21) Appl. No.: 16/245,806

(22) Filed: Jan. 11, 2019

(65) Prior Publication Data
US 2019/0239938 A1    Aug. 8, 2019

(30) Foreign Application Priority Data

Feb. 5, 2018    (EP) .................................... 18155037

(51) Int. Cl.
*A61B 18/20*    (2006.01)
*A61B 18/02*    (2006.01)
(Continued)

(52) U.S. Cl.
CPC ........ *A61B 18/0218* (2013.01); *A61B 18/203* (2013.01); *A61C 1/0046* (2013.01);
(Continued)

(58) Field of Classification Search
CPC .............. A61B 18/0218; A61B 18/203; A61B 2090/049; A61B 2018/00005;
(Continued)

(56) References Cited

U.S. PATENT DOCUMENTS 5,846,235 A * 12/1998 Pasricha ............ A61B 18/0218
606/23
6,451,007 B1 * 9/2002 Koop ..................... A61B 18/20
128/898
(Continued)

FOREIGN PATENT DOCUMENTS

KR    10-2010-0054097    5/2010
KR    10-2016-0146337    12/2016
(Continued)

OTHER PUBLICATIONS

European Search Report for corresponding European Patent Application No. 18155037.7 dated Aug. 20, 2018.
(Continued)

*Primary Examiner* — Ankit D Tejani
*Assistant Examiner* — Joshua Brendon Solomon
(74) *Attorney, Agent, or Firm* — Renner, Otto, Boisselle & Sklar, LLP

(57)    ABSTRACT

An apparatus for cooling tissues which are treated with an energy-based device, such as a laser, is disclosed. The apparatus comprises a spray nozzle which generates an atomized liquid spray for the treatment area, wherein the atomized liquid spray is based on a mixture of liquid and gas. Further, the spray nozzle comprises at least one liquid outlet which ejects a liquid, and at least one gas outlet which ejects a gas stream. Besides, the apparatus for cooling comprises at least one delivery means for delivering pressurized gas to the spray nozzle; and a pumping means for the liquid, wherein the pumping means is configured to operate in pulses.

14 Claims, 6 Drawing Sheets

Figure 1:
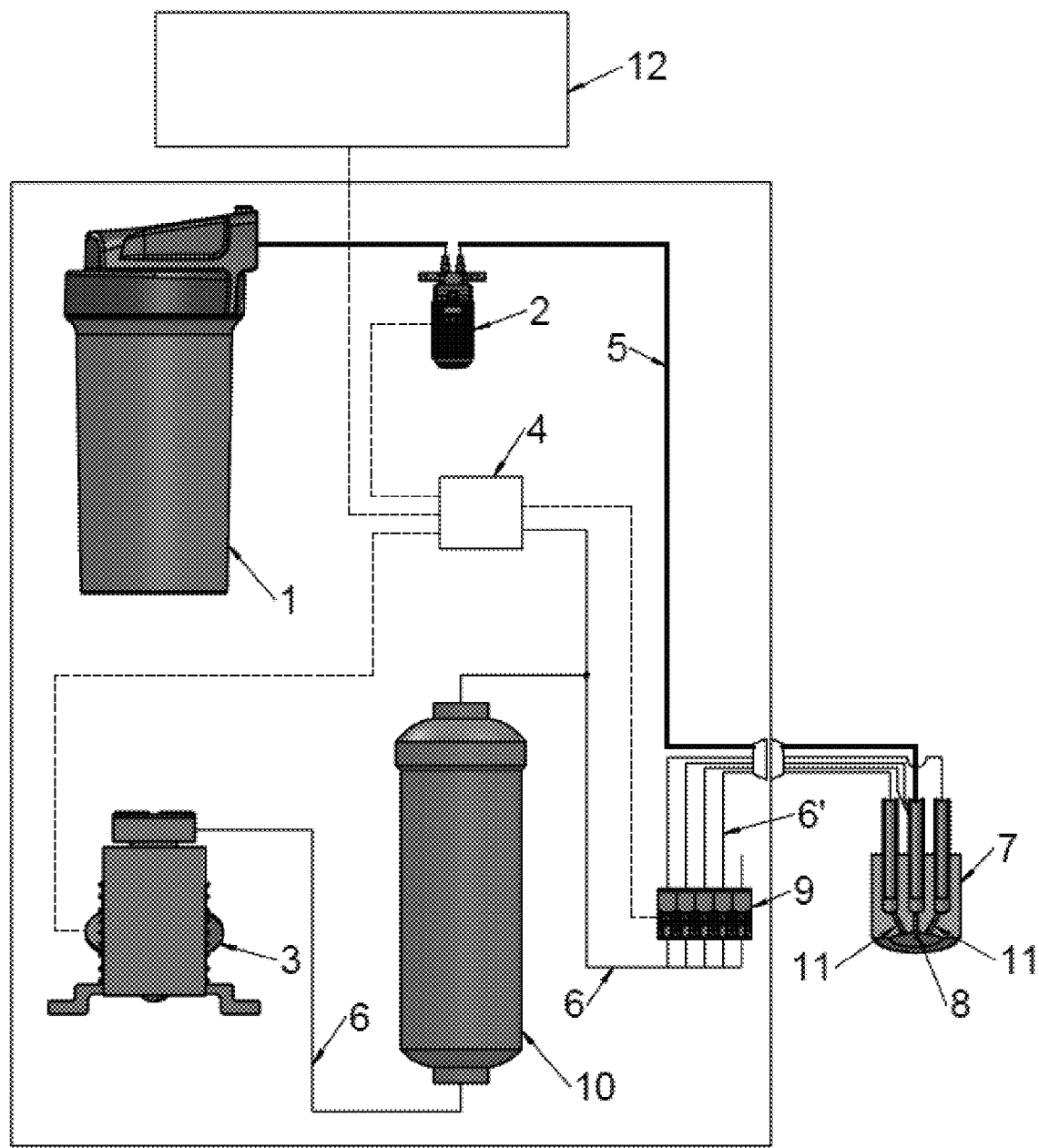

(51) Int. Cl.
*A61C 1/00* (2006.01)
*A61N 5/06* (2006.01)
*A61C 17/028* (2006.01)
*A61B 18/00* (2006.01)
*A61B 90/00* (2016.01)

(52) U.S. Cl.
CPC .......... *A61C 1/0061* (2013.01); *A61C 17/028* (2013.01); *A61N 5/0616* (2013.01); *A61B 2018/00005* (2013.01); *A61B 2018/00029* (2013.01); *A61B 2018/00452* (2013.01); *A61B 2090/049* (2016.02)

(58) Field of Classification Search
CPC .......... A61B 2018/00029; A61B 2018/00452; A61C 1/0046; A61C 1/0061; A61C 17/028; A61N 5/0616
See application file for complete search history.

(56) References Cited

U.S. PATENT DOCUMENTS

| | | | | |
|---|---|---|---|---|
| 6,709,269 | B1* | 3/2004 | Altshuler | A61C 1/0046 433/215 |
| 2003/0139735 | A1* | 7/2003 | Neuberger | A61B 18/20 606/3 |
| 2004/0065846 | A1* | 4/2004 | Yamazaki | A61B 18/203 250/492.1 |
| 2008/0215040 | A1* | 9/2008 | Paithankar | A61B 18/203 606/9 |
| 2010/0121418 | A1 | 5/2010 | Lee et al. | |
| 2011/0160712 | A1* | 6/2011 | Tankovich | A61B 18/203 606/9 |
| 2013/0323672 | A1* | 12/2013 | Monty | A61C 1/0069 433/29 |
| 2015/0351822 | A1* | 12/2015 | Mulcahey | A61B 90/98 606/22 |
| 2017/0231655 | A1* | 8/2017 | Aljuri | A61B 17/3203 606/170 |
| 2018/0214207 | A1* | 8/2018 | Deibel | A61B 18/20 |

FOREIGN PATENT DOCUMENTS

| | | |
|---|---|---|
| WO | 99/27863 | 6/1999 |
| WO | 99/39652 | 8/1999 |
| WO | 2006/063334 A2 | 6/2006 |

OTHER PUBLICATIONS

Korean Notice of Grounds for Rejection and English translation for corresponding Korean Patent Application No. 10-2019-0012571 dated May 11, 2020.

* cited by examiner

MICRO-PULSED LIQUID SPRAY FOR COOLING

This application claims priority to European Patent Application No. 18155037.7 filed on Feb. 5, 2018, which is hereby incorporated herein by reference.

FIELD OF THE INVENTION

The present invention relates to a system and a method for cooling surfaces, in particular for cooling surfaces of human or animal tissues which are treated with an energy-based medical device such as a laser, an intense pulse light (IPL) device or a radio frequency (rf) device.

TECHNICAL BACKGROUND

In the following, only medical and biological applications will be discussed but the invention is also directed towards industrial or other applications where a fast cooling of surfaces is required.

In medical applications where energy is delivered to the tissue for heating, coagulation or destruction of targets, a non-specific heating of the tissue surface (such as the epidermis) is a common side effect. Energy-based medical devices include, for example, a laser, an intense pulse light (IPL) device or a radio frequency (rf) device. In what follows, the words "laser", "laser pulse", "laser beam" etc. will be used from time to time to represent any type of such energy-based devices.

In treatments using energy-based medical devices, a certain amount of energy needs to be delivered, in order to achieve the desired effect on the target chromophore or target structure. For example, in applications for hair removal by means of a laser, enough laser fluence (energy/area) needs to be delivered to the hair bulb, in order to achieve its destruction, but, at the same time, the epidermal damage should be minimized. As many laser wavelengths, especially the ones which penetrate the skin surface, are absorbed in melanin (which is abundantly present in the epidermis), heating of the epidermis is an inevitable side effect of many laser treatments. Often, the threshold fluence which is needed for destroying the target chromophore or structure is very close to the fluence threshold for epidermal injury. Besides, uncontrolled heating of the epidermis above its coagulation temperature of 65 to 70° C. for a prolonged period of time can induce acute epidermal damage or blistering and can also lead to scarring and hypopigmentation. In order to avoid these complications, while at the same time allowing enough energy to be delivered to the target structure, cooling of the epidermal surface layer is necessary.

Exemplary applications where high energies are used and cooling is necessary for avoiding epidermal damage include laser hair removal, coagulation of veins and vascular lesions. In other applications, e.g. non-invasive fat reduction, relatively low energy densities are delivered during a prolonged exposure to a laser, a radio frequency device, or another energy source which leads to a prolonged heating of the subdermal fat to temperatures above 42° C. This causes an apoptosis of adipose cells and a reduction of the fat layer. In these methods, epidermal cooling may be used for avoiding a prolonged heating of the epidermis, thus maximizing patient safety and comfort.

In treatments with energy-based medical devices, the problem of epidermal overheating is overcome by cooling the epidermis prior, during and/or after the treatment. An ideal cooling method should efficiently lower the temperature of the epidermal surface layer only, since a cooling of deeper layers would interfere with the desired heating of the target structure/chromophore. In particular, if deeper layers of the tissue were also cooled, it would be necessary to deliver higher energies to the target structure/chromophore for obtaining the desired temperature.

Different types of cooling systems are regularly used in medical systems, wherein different types of cooling mediums are brought in contact with the tissue surface. The most common methods include contact cooling with a chilled surface of a cooling device, cooling by means of a cryogen spray and cooling with cold air.

Contact cooling using a cooled glass or metal surface is commonly used and achieves a localized and rapid cooling. However, this method is disadvantageous, if cooling is needed for a prolonged period of time, since the prolonged exposure to a cold plate (which is normally kept at a low temperature by an active delivery of another cooling media such as a liquid coolant) leads to the cooling of deeper tissue layers and of the target structure. However, as already mentioned above, the cooling of deeper layers leads to an increase of the energy needed for target destruction. Besides, contact cooling methods can also result in skin compression which, in some application, influences the absorption of the target chromophore, e.g., in the case of the removal of vascular lesions.

Cooling by means of a cryogen spray is another commonly used method. In this cooling method, a cryogen spray is sprayed shortly before the delivery of the laser pulse, thus minimizing the exposure of the skin to the cryogen spray which cools to very low temperatures. This method is efficient for epidermal protection when high fluences are used. However, side effects from excessive skin cooling, such as hypopigmentation and skin irritations, have been reported. Besides, a cryogen spray is also harmful to the environment, since it has a high global warming potential.

Cold air cooling is often used in laser treatments, wherein the cold air is directed to the treatment area before and during the laser treatment. The disadvantage of air cooling is the relative inefficiency of the medium air for cooling tissues, thus requiring long exposure times to cold air. This can lead to patient discomfort and to the cooling of deeper layers (which, as mentioned before, impacts the threshold fluence needed for the destruction of the target chromophore).

A water-based spray has been commonly used in dental laser applications, mainly for moistening the tissues, debris removal and as an aid for a more efficient ablation. However, a water-based spray has not been used for cooling tissue surfaces, especially not for cooling skin surfaces. The reason for this is that the commonly available liquid sprays, such as the ones used by dental lasers, operate continuously and hence would generate a liquid film on the skin surface which would act as a thermal barrier for the heat transfer. In particular, if a liquid film is present, a quick evaporation of liquid droplets can no longer take place, thus preventing an efficient cooling. To avoid the formation of an undesirable liquid film. the liquid has to be in constant flow. In particular, the liquid has to be constantly removed from the treatment area. A removal of the liquid by means of a suction device can be relatively easily achieved in an enclosed treatment area which is already wet, such as the mouth, but becomes very impractical when trying to cool large body surfaces. In addition, in many dermatological applications such as hair removal, skin tightening and fat reduction, an effective and homogeneous cooling of large skin areas of up to about 5000 cm² is required which represents a considerable technical challenge when liquid spray cooling is used.

The present invention is concerned with a device and a method for cooling tissues that are treated with an energy-based medical device, wherein at least some of the above-described disadvantages of the prior art are avoided.

SUMMARY OF THE INVENTION

According to one aspect of the present invention, an apparatus for cooling comprises a spray nozzle which generates an atomized liquid spray for the treatment area, wherein the atomized liquid spray is based on a mixture of liquid and gas; at least one delivery means for delivering pressurized gas to the spray nozzle; and a pumping means for the liquid, wherein the pumping means is configured to operate in pulses.

It should be noted that a pulsed application of the spray to the tissue has the advantage that, in between two subsequent pulses, the evaporation of the droplets can take place on the tissue surface, thus avoiding a wet tissue/skin. Further, the apparatus for cooling tissues is operated in such a way to achieve a fine "micro-pulsed" liquid spray with optimal liquid content, droplet size and velocity which together enable quick evaporation of the droplets and quick cooling of the tissue surface.

The spray which is applied to the tissue consists of a mixture of a liquid and a gas. The gas may consist of air, but may also be any other suitable gas or gas mixture which is not inflammable or harmful to humans. In what follows the word "air" will be used from time to time to represent a gas in general (not limited only to air). An example of another suitable gas besides air is nitrogen. Similarly, the liquid may be water, but may be also any other suitable liquid, liquid mixture or solution that is not inflammable or harmful to patients.

According to another aspect of the present invention, the spray nozzle of the apparatus for cooling comprises at least one liquid outlet which ejects a liquid; and at least one gas outlet which ejects a gas stream.

Thus, the liquid spray is generated by using separate outlets for the liquid and the gas. Accordingly, the spray is generated outside the nozzle when the gas stream (gas jet) ejected from the gas outlet impinges on the liquid drops which are ejected from the liquid outlet. Due to the collision of the gas and the liquid, the liquid is atomized into small liquid droplets which form the spray.

The ratio of the fluid to the gas in the spray is important for achieving the optimal liquid content in the spray. The ratio of the liquid to the gas in the spray is regulated by controlling the liquid flow from the liquid outlet and/or the gas flow from the gas outlet.

Preferably, the apparatus is configured in such a way that the gas which is ejected from the gas outlet determines the direction of motion of said atomized liquid spray.

Thus, the gas stream (which has a certain direction of motion when being emitted from the gas outlet) takes along the liquid (which is output from the liquid outlet) so that the generated liquid spray has the direction of the gas stream. This way, the direction into which cooling spray moves can be controlled by controlling the direction of motion of the emitted gas stream. Consequently, the region on the tissue surface where the cooling spray is applied is also determined by the direction of the emitted gas stream. It is further noted that the geometry of the gas outlet, in particular its orientation within three-dimensional space, determines the direction of the gas stream which is ejected from the gas outlet. This way, a precise control of the location on the tissue surface where the liquid spray is applied is possible.

Without the source of the gas flow, the liquid would exit the liquid outlet in the form of large liquid droplets or a drizzle (considering the small levels of liquid flows which are preferably used). As noted above, if there exists a gas flow near the liquid outlet opening, these liquid droplets are carried away by the gas flow in the form of a mist, wherein the spatial distribution of the mist follows approximately the spatial distribution of the gas flow. Typically, the spray has the form of a cone which extends from the gas nozzle exit to the surface to be cooled.

In certain embodiments, the gas pressure within the gas delivery means of the apparatus is in the range from 0.1 to 10 bar, preferably from 1 to 5 bar.

Such levels for the gas pressure are beneficial for the effect that the gas stream from the gas outlet has enough force to take along the liquid droplets from the liquid outlet so that the direction of the generated liquid spray essentially follows the direction of the gas stream.

Preferably, the liquid is ejected from the liquid outlet with a low pressure in the range from 0.1 to 0.5 bar.

The low pressure of the liquid (and a correspondingly low velocity of the liquid particles) is also beneficial for the effect that the gas stream from the gas outlet determines the direction of motion of the generated spray. Besides, a low pressure helps in avoiding a dripping of the liquid when the spray nozzle is turned off.

Preferably, the liquid flow through the pumping means of the apparatus is in the range from 0.001 to 10 ml/min, more preferably from 0.2 to 2 ml/min.

First, it is noted that the liquid flow (i.e., the liquid volume per unit time) which is ejected from the liquid outlet corresponds to the liquid flow through the pumping means (due to the conservation of mass). Using liquid flows in the above-specified range is beneficial for the effective cooling of the tissue surface area by means of the fast evaporation of liquid droplets of the spray. On the one hand, such a liquid flow leads to the result that a sufficient number of liquid droplets are deposited onto the tissue area, in order to provide a cooling effect. On the other hand, when using such a liquid flow the number of liquid droplets is not so high that a liquid film is formed. As noted above, such a liquid film is undesirable, since it would effectively reduce the liquid evaporation rate and would also cause an uncomfortable and undesirable over-wetting of the patient.

Further, it should be noted that the above-mentioned pulsed operation of the pump for the liquid leads to a good control of the liquid flow, as the frequency of the pulses can be varied.

In certain embodiments, the liquid outlet has an orifice, wherein this orifice has a diameter from 0.1 to 1 mm, preferably from 0.3 to 0.5 mm.

The above-specified range for the pressure and the above-specified range for the flow of the liquid are compatible with an orifice which has a rather large diameter. Thus, the problems when using orifices with a small diameter (i.e., in the order of several microns) are avoided. In particular, orifices with a small diameter get very quickly clogged, i.e., temporarily by small gas bubbles which are always present in flowing liquids, and, in the long term, by the sediments and impurities within the liquid.

In certain embodiments, the pumping means operates with a frequency from 0.1 to 1 kHz, preferably from 0.5 to 50 Hz.

For achieving the above-specified small liquid flows, a positive displacement fluid pump can be used. Positive displacement pumps draw the fluid into a compartment at the inlet of the pump and move the fluid to the outlet for discharge. A positive displacement pump moves the liquid at the same speed regardless of the pressure on the inlet end. Positive displacement pumps can be classified according to the method which moves the liquid, namely a rotary or an oscillating (reciprocating) method. However, it is noted that rotary positive displacement pumps are relatively complicated. Moreover, an oscillating positive displacement pump has the advantage that its naturally lends itself to a pulsed operation. Thus, an oscillating positive displacement pump is a preferred embodiment for the pumping means of the present apparatus for tissue cooling.

A diaphragm pump which is a sub-class of the oscillating positive displacement pumps is an even more preferred embodiment for the pumping means of the apparatus.

In certain embodiments, the liquid comprises one or more of the following additives: a solution which enhances the evaporation rate, a solution which conditions the skin, a solution for aromatherapy, and a disinfecting solution.

It is noted that the liquid may be water, but may also be any other suitable liquid or liquid mixture or solution which is not inflammable or harmful to patients. For example, a water alcohol solution may be used, provided that the alcohol concentration does not exceed the concentration of about 50% at which point the solution becomes inflammable, especially under laser irradiation. Adding rapidly evaporating liquids such as alcohol to the fluid speeds up the evaporation of the liquid droplets of the spray, and hence enhances the cooling rate.

Other additives can be mixed into the spray as well, in order to support moisturizing, a faster healing, disinfection, pain reduction, or the creation of a more pleasant aroma. One of the preferred embodiments involves adding substances to the fluid, gas or to both which cover most effectively the undesirable odour which, for example, results from laser ablation of human tissues.

Preferably, the size of the droplets of the atomized liquid spray which is generated by the apparatus for cooling tissues is in the range from 5 to 200 micrometers, more preferably from 10 to 100 micrometers.

It is noted that the droplets need to be small enough to evaporate when being in contact with the treated skin so that a fusing of the droplets and the formation of a liquid film on the skin surface is avoided. As already mentioned, such a liquid film lowers the heat transfer rate from the skin to the liquid medium. On the other hand, the droplets need to be sufficiently large for sticking to the skin surface and for enabling the heat transfer from the epidermis to the cooling medium. It is also noted that the size of the droplets is influenced by the size of the orifice of the liquid outlet.

In certain embodiments, the spray nozzle comprises one liquid outlet in combination with a plurality of gas outlets.

By using a nozzle having a plurality of gas outlets near one liquid outlet, the generated liquid spray can be directed to different regions on the tissue surface (without moving the apparatus for cooling tissues itself). Namely, each gas outlet has a different direction into which the gas is ejected. Since the gas takes along the liquid droplets when the spray is generated, the different directions into which the gas outlets point correspond to different regions on the tissue surface where the spray is applied. A plurality of gas outlets is particularly helpful if the cooling spray shall cover a relatively large tissue surface (e.g., a large area of the skin), since switching between the various gas outlets is generally faster than changing the orientation of a single gas outlet.

Preferably, each one of the plurality of gas outlets (which surround a single liquid outlet) has a corresponding delivery means.

The feature that each of said plurality of gas outlets has its proper delivery means for the gas (e.g., a gas tube) is helpful for the independent operation of each gas outlet, i.e. the operation of one gas outlet should not interfere with the operation of another gas outlet.

Thus, preferably, the gas flow from each one of the plurality of gas outlets can be controlled independently of the other gas outlets.

Further preferably, the apparatus for cooling is configured in such a way that the various gas outlets operate sequentially, i.e., only one gas outlet is active at a time. This is beneficial for the control of the direction of motion of the generated spray. In particular, the direction of the generated spray would be largely undetermined, if two or more gas streams (with each one having a different direction of motions) hit the liquid drops from the liquid outlet at the same time.

According to another aspect, the apparatus for cooling can be integrated into the handpiece of a laser system. This way, the spray pulses which are generated by the apparatus for cooling can be easily applied at or near the treatment area which is irradiated by the laser pulses, wherein these laser pulses are emitted from the handpiece of the laser system. Similar considerations apply to other energy-based medical devices.

Preferably, a device which ejects a jet of cold air is additionally mounted on the handpiece of the laser piece. The cold air which is ejected from this device can provide an additional cooling effect for the treated tissue (in addition to the cooling by means of the spray). In particular, as discussed in more detail below, there is a synergistic effect between the cooling by means of cold air and the cooling by means of the liquid spray, since the achieved cooling effect (measured as the drop of temperature of the cooled tissue) when both the spray and the cold air are applied is greater than the sum of the cooling effects for the spray and the cold air.

Preferably, the temperature of the cold air is in the range from $-40°$ C. to ° C., more preferably from $-35°$ C. to $-20°$ C.

According to another aspect, the apparatus for cooling is mounted on the scanning device of a laser scanner. Such laser scanners are often used for the treatment of large areas, e.g. the skin of a human or animal.

Further preferred embodiments are described in the appended dependent claims.

It is noted that any combination of features that have been described above as belonging to certain embodiments/aspects of the present invention is also an embodiment of the present invention, if such a feature combination is feasible, i.e., does not lead to a contradiction.

DETAILED DESCRIPTION OF PREFERRED EMBODIMENTS

Figure 2:
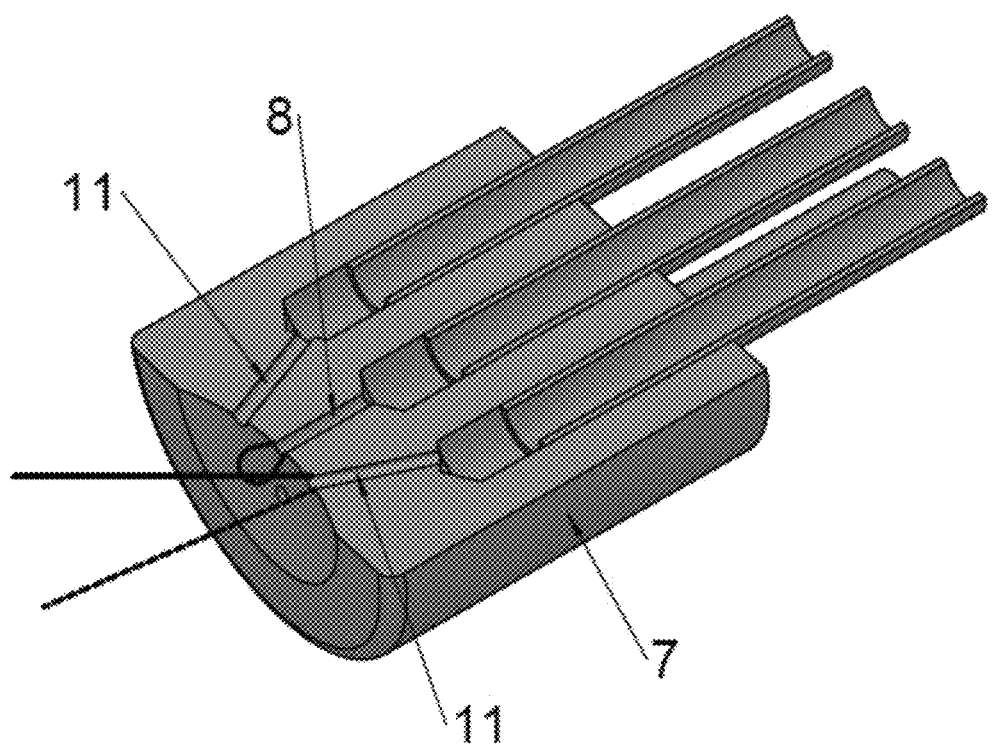
Figure 3:
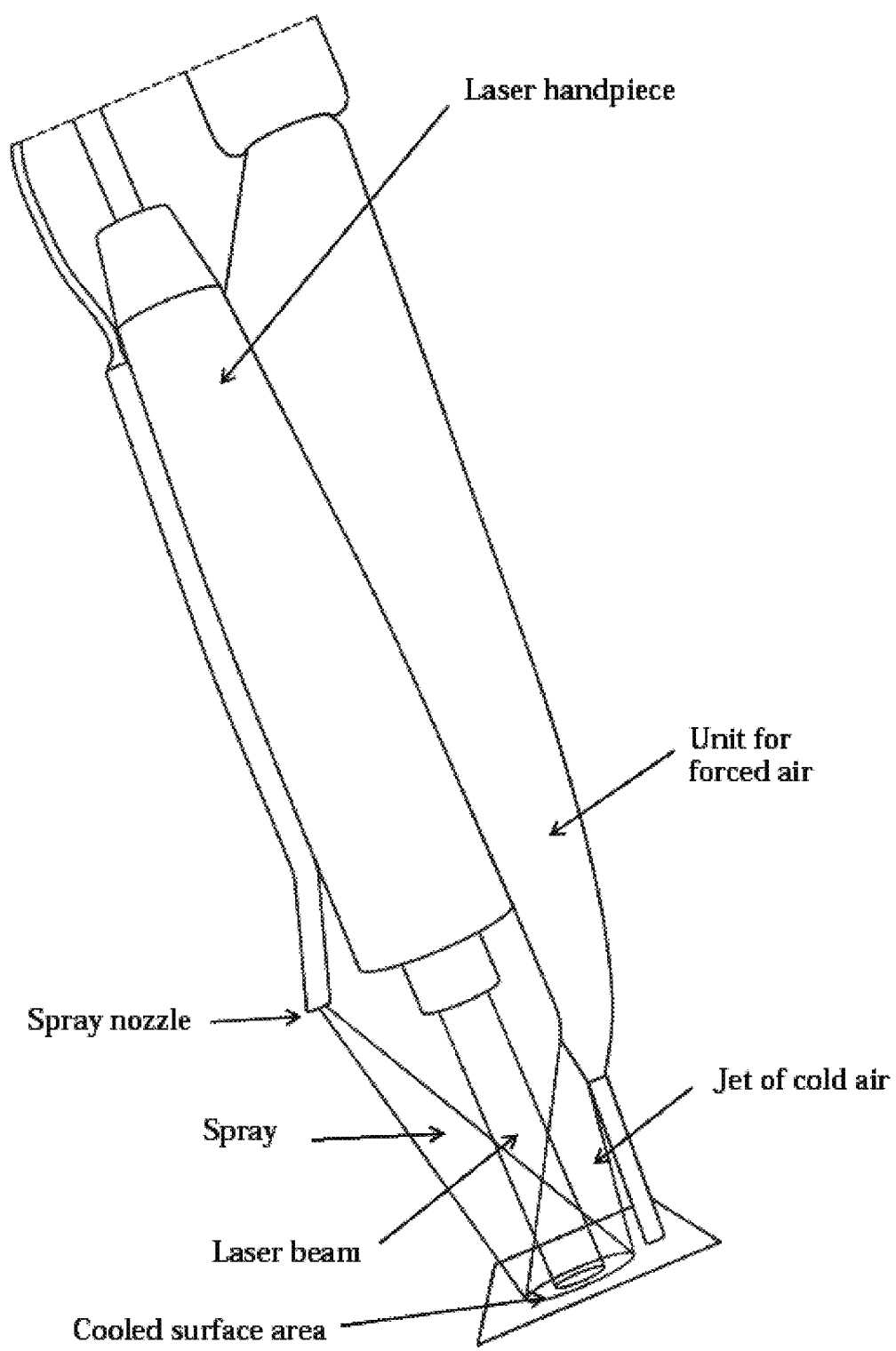
Figure 4:
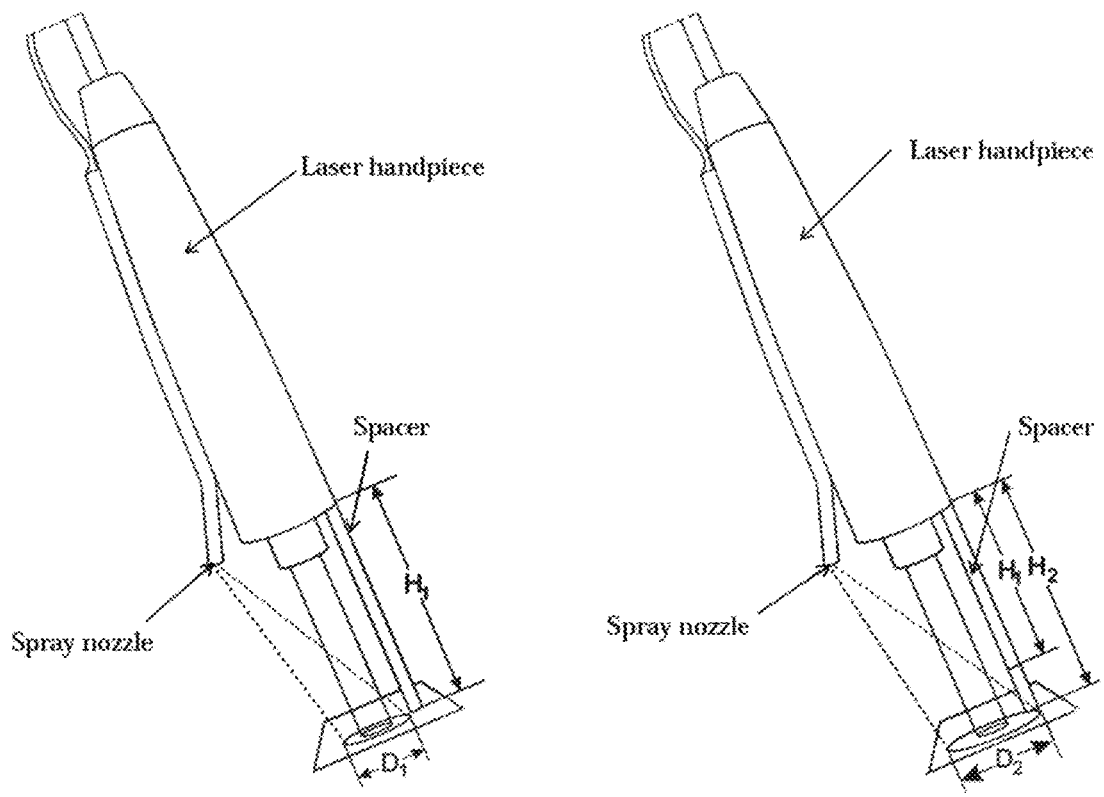
Figure 5:
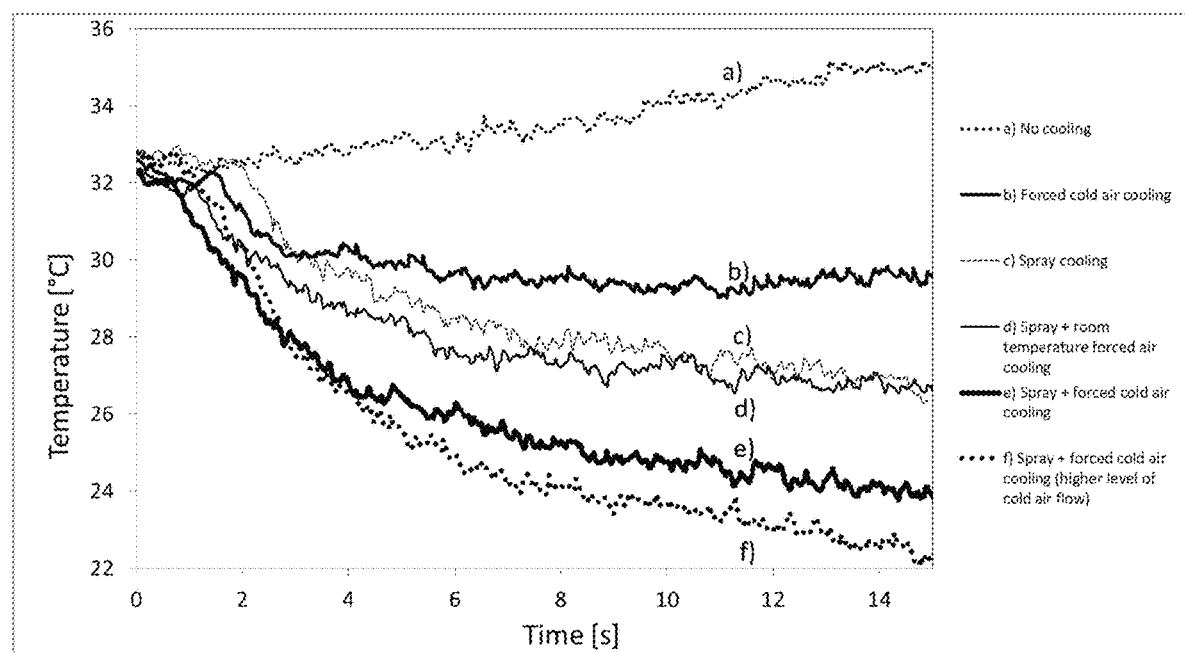
Figure 6:
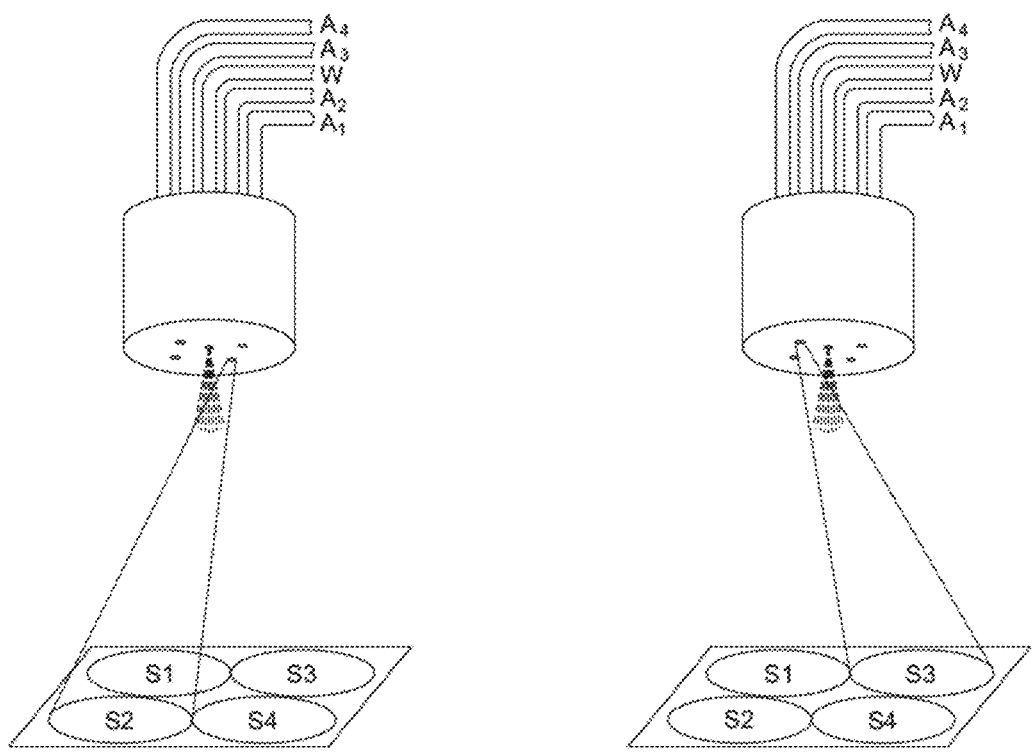

Some of the embodiments of the invention will be explained in the following with the aid of the Figures in more detail. It is shown in:

FIG. 1 an apparatus for cooling tissues according to the present invention;

FIG. 2 a spray nozzle which comprises one liquid outlet and four gas outlets;

FIG. 3 a laser handpiece to which apparatus for cooling tissues according to the present invention is attached;

FIG. 4 a schematic view how the area to which the spray is applied can be varied by changing the distance between the spray nozzle and the tissue surface;

FIG. 5 a comparison of the measured skin surface temperature under laser irradiation when 6 different cooling methods are used;

FIG. 6 a schematic view of a spray nozzle which combines a single liquid outlet with four gas outlets.

FIG. 1 illustrates an apparatus 100 for cooling tissues which comprises a liquid reservoir 1, a pumping means 2, a gas reservoir 100, a gas compressor 3, gas valves 9 and a gas pressure regulator 4. Apparatus 100 further comprises delivery means 5 for the liquid and delivery means 6 for the gas, wherein these delivery means combine within a spray nozzle 7.

Delivery means 5 having the form of a tube delivers the liquid from liquid reservoir 1 to spray nozzle 7, wherein the flow of the liquid is regulated by pumping means 2. In the embodiment of FIG. 1, pumping means 2 is a low pressure pump (for example, a diaphragm pump). The low pressure pump works in a pulsed mode with frequencies in the range from 0.1 to 1 kHz, preferably from 0.5 to 50 Hz.

Delivery means 6 for the gas also has the form of a tube and delivers gas from gas reservoir 10 through gas compressor 3 to spray nozzle 7, wherein gas compressor 3 is used for regulating the gas pressure. In the apparatus of FIG. 1, the gas pressure is in the range from 1 to 5 bar.

It is noted that FIG. 1 shows a plurality of gas valves 9 which correspond to a plurality of gas outlets 11 within spray nozzle 7. This way, by opening and closing the various gas valves 9, it can be controlled which gas outlet 11 ejects the gas at a certain moment.

Further, by controlling the gas valves 9 and activating specific gas outlets 11, the direction of movement of the spray which is ejected from nozzle 7 can be determined.

It is noted that, according to FIG. 1, pumping means 2, gas compressor 3 and gas valves 9 are connected to spray controller 4. Thus, spray controller 4 can control the amounts of liquid and gas which are delivered to spray nozzle 7 as well as the pressures under which liquid and gas are delivered.

Spray controller 4 itself is connected to computer control means 12 of the energy-based device so that synchronisation of the pulsed spray operation with the pulses of the energy-based device is possible.

It is further noted that the amount of liquid in the spray, the liquid/gas ratio and the droplet size are important factors for achieving an optimal evaporation cooling for the epidermal surface. Here, the amount of liquid in the spray may be regulated by a pulsed operation of pump means 2 or by regulating the pressure in liquid reservoir 1. In particular, pumping frequencies between 1 and 20 Hz have been used for obtaining a suitable liquid content for the spray, wherein the liquid flow rates are between 0.05 and 10 ml/min, more preferred between 0.2 and 2 ml/min.

The gas/liquid ratio can be regulated through the combined regulation of pumping means 2 and the gas pressure from gas reservoir 10 (cf. FIG. 1). The gas pressure for achieving a suitable gas/liquid ratio of the spray is in the range from 0.1 to 10 bar, preferably from 1 to 5 bar. The corresponding liquid flow density of the spray is in the range from 0.001 to 2 ml/(min×cm$^2$), preferably in the range from 0.002 to 0.5 ml/(min×cm$^2$). This ensures that, on one hand, there is a sufficient number of sufficiently small liquid droplets being deposited onto the cooled surface area and, on the other hand, the number of liquid droplets is not too high, thus avoiding the formation of a liquid film (which would effectively reduce the liquid evaporation rate and cause an uncomfortable and undesirable over-wetting of the patient, of the bed and of the surrounding).

As noted above, liquid flows LF (in ml/min) for typical treatment areas and cooling times are in the range of 0.001 to 10 ml/min. These are very small liquid flows which are technically very challenging to achieve in a reliable manner. In particular, a positive displacement pump can be used within the apparatus for cooling according to FIG. 1.

Positive displacement pumps draw the fluid into a compartment at the inlet of the pump and move the fluid to the outlet for discharge, wherein the liquid has the same speed regardless of the pressure at the inlet end. Such positive displacement pumps can be classified according to the method which is used for moving the liquid, namely a rotary or an oscillating (reciprocating) method. However, rotary positive displacement pumps are relatively complicated. Moreover, an oscillating positive displacement pump has the advantage that it naturally lends itself to a pulsed operation. Thus, an oscillating positive displacement pump, in particular a diaphragm pump, is used for pumping means 2 according to FIG. 1. By operating these low pressure pumps in pulses, the level of the liquid flow can be precisely regulated.

Due to the low liquid flow and the low liquid pressure, relatively large orifices of the liquid outlet 8 of spray nozzle 7 can be used. In particular, the diameter of the orifice can be in the range from 0.1 to 1.0 mm.

FIG. 2 shows a view of spray nozzle 7, wherein the spray nozzle comprises one liquid outlet 8 and four gas outlets 11 (two of them are shown sliced). The liquid and gas outlets are arranged in such a way that the resulting spray cloud can be directed towards different regions of the treatment area. When using the spray nozzle according to FIG. 2, the liquid stream from liquid outlet 8 and the gas stream from one of gas outlets 11 are mixed externally, in order to generate an atomized liquid spray.

FIG. 3 illustrates a laser handpiece to which an apparatus for cooling tissues according to the present invention is attached. It is noted that the laser system comprises a laser system body, a laser delivery means (e.g. an articulated arm or an optical fiber), and the handpiece (as shown in FIG. 3), wherein the handpiece is connected to the distal end of the laser delivery means. The optics and configuration of the handpiece determines the shape and size of the laser-irradiated area. Both the pumping means and the gas pressure regulator/gas compressor of the cooling apparatus are connected to the computer control means of the laser system. This way, a synchronisation of the pulsed spray operation with the emitted laser pulses is possible.

As can be seen in FIG. 3, a spray is ejected from the spray nozzle, wherein the transversal cross-section of the ejected spray successively widens so that the spray jet has the form of a cone. It is noted that the spray is directed to the treatment area on the tissue surface, i.e., the area on the tissue surface to which the spray is directed essentially corresponds to the spot size of the laser beam which is emitted from the hand piece. Thus, if spray and laser pulses are synchronized, the spray cooling of the tissue can take place simultaneously with the laser treatment of the tissue.

For the gas pressure and nozzle parameters as above, we have discovered that the cone angle of the generated spray cannot be increased significantly above approximately 20° (see FIG. 3). The cone angle and the distance between spray nozzle and treatment area determine the surface area where a spray pulse is applied (this surface area is simultaneously cooled by the spray). For example, if a distance H from the gas nozzle to the surface to be cooled is H=20 cm, the diameter $D_1$ of the area which cooled is approximately equal to $D_1$ 0.7 cm, wherein the diameter $D_0$ that corresponds to a central part which is relatively homogenously cooled is $D_0 \approx 3$ cm.

The size of the area to which the spray is applied can be adjusted to the size of the treatment area by adjusting the height H as shown in FIG. 4. In particular, FIG. 4 shows that the area on the tissue surface to which the spray is applied increases, if the height H1 is increased to H2. More generally, the area to which the spray is applied can be modified by changing the height and/or the angle of the nozzle relative to the tissue.

In some embodiments of the invention, the height H of the spray nozzle above the treatment area is controlled by a spacer of a certain length, wherein the spacer can be mounted to the laser handpiece and wherein the length of the spacer can be changed by operating a mechanism. As can be seen in FIG. 4, a spacer of a certain length contacts the skin surface (in the surroundings of the treatment area) and hence keeps the distance between the nozzle and the tissue surface constant (i.e., the value H is kept constant). In the two parts of FIG. 4, the length of the spacer is increased from H1 to H2 so that the height of the nozzle above the treatment area is increased as well. In yet another embodiment of the invention, the angle of the spray nozzle relative to the tissue can be regulated by adjusting a joint-type element between the spray nozzle and the body of the laser handpiece.

FIG. 3 also shows a unit which ejects a stream of cold air, wherein this unit is also attached to the laser handpiece. The stream of cold air is directed to the treatment area and thus has a cooling effect for the treatment area (in addition to the cooling spray from the spray nozzle). It is noted that, in FIG. 3, a spacer is mounted to the unit for cold air.

In order to quantify this additional cooling effect, FIG. 5 shows a comparison of the measured skin surface temperature under laser irradiation, wherein FIG. 5 displays line a: no cooling;
line b: forced cold air cooling using a commercial Cryo 6 device (manufactured by Zimmer);
line c: micro-pulsed spray cooling according to the present invention;
line d: micro-pulsed spray cooling according to the present invention combined with forced air cooling (air has room temperature); and
lines e, f) micro-pulsed spray cooling according to the present invention combined with forced air cooling (cold air from Cryo 5 device) for two different levels of the cold air flow.

As can be seen from FIG. 5, the inventive micro-pulsed spray cooling is significantly faster (cf. line c) than the commonly used forced cold air cooling (cf. line b). We have also found out that the cooling rate of the micro-pulsed spray cooling can be additionally increased by directing an additional forced cold air flow to the treated area (cf. lines e and f). On the other hand, an additional forced air flow at room temperature does not significantly contribute to the cooling rate (cf. line d).

Sometimes, large areas of the human tissue must be irradiated, for example during a hair removal procedure where a handpiece with a large spot size of the laser beam or a canning device is used. Then, the above-shown application area of the spray with diameter $D_0$ may be too small. Besides, it may be desirable that the laser beam is moved over a treatment area such that a pre-cooling is performed, i.e. a tissue area is cooled before being irradiated. Similarly, it may be advantageous to post-cool a tissue area that has been irradiated. Alternatively, it may be advantageous to be able to pre-cool, cool and post-cool the treated tissue when moving the laser beam across the treatment area.

In such cases, a "scanning micro-pulse spray apparatus" according to the present invention can be used where at least one liquid outlet is combined with a multiplicity of gas outlets, wherein each gas outlet is directed to a different region of the tissue area. By switching the ejected gas stream successively from one gas outlet to another one, it is possible to achieve relatively homogeneous spray coverage of large skin areas.

FIG. 6 shows a schematic view of a spray nozzle where a single liquid outlet is surrounded by four gas outlets. In this embodiment, the liquid outlet is connected to a liquid input W, and the gas outlets are connected to corresponding gas inputs A1, A2, A3 and A4. There is a single source of pressurized gas which is connected to the A1, A2, A3 and A4 gas lines by means of four separate gas valves. By closing and opening these gas valves, it is possible to change the area which is cooled by the spray. For example, if the laser scanner is adjusted to scan the laser beam only over areas S3 and S4 (as shown in FIG. 6), the gas valves may be controlled in such a manner that the spray is directed only to areas S3 and S4. In another embodiment, the cooled area may be synchronized with the laser scanner in such a manner that the area which is predominantly cooled tracks the area which is currently irradiated. Thus, if the scanned laser beam proceeds from Si to S4 during the scan, so does the scanned micro-pulsed spray.

In yet another preferred embodiment, the fluid spray may alternate among the plurality of valves in such a manner that either a pre-cooling or a post cooling or both are performed for the treated tissue when moving the laser beam across the treatment area. Generally, the pre-cooling and/or post cooling are performed at a time difference when compared with the cooling of the treatment area. Alternatively, the spray nozzle with a plurality of gas outlets may be operated in such a manner that only the pre-cooling or the post-cooling or both are performed, but that no spray is applied to the area currently being irradiated.

In general, by closing and opening the gas valves for the gas outlets, it is possible to control the rate at which the spray is applied to an area and to select the part of the tissue surface which is cooled.

Further, the operation of the cooling mechanism, the amount of liquid, the gas/liquid ratio can be adjusted in response to the recorded temperature of the tissue after the treatment, wherein this temperature can be recorded using a temperature detector. The temperature detector could be also integrated into a thermal camera which would provide an additional visual aid for the laser operator.

Finally, the apparatus for cooling tissues according to the present invention which generates the micro-pulsed spray can be designed as a stand-alone unit which may be used together with different energy-based devices, or it may be integrated into a particular energy-based device. Further, the apparatus for cooling may be operated independently from the energy-based device, or it may be configured to receive certain control signals from the energy-based device. In the latter case, the release of the spray pulses from the apparatus for cooling can occur, for example, in synchronization (with respect to time and/or treatment area) with the delivery of the treatment energy.

The invention claimed is:

1. An apparatus for cooling tissues which are treated with an energy-based device, such as a laser, the apparatus comprising:

a spray nozzle which generates an atomized liquid spray for the treatment area, wherein the atomized liquid spray is based on a mixture of liquid and gas, wherein said spray nozzle comprises at least one liquid outlet which ejects a liquid in the form of liquid droplets, and at least one gas outlet which ejects a gas stream, wherein the at least one liquid outlet is spatially separated from the at least one gas outlet and arranged such that the gas stream ejected from the at least one gas outlet will intersect and interact with the liquid droplets ejected from the at least one liquid outlet, such that the liquid droplets are carried away by the gas stream to generate the atomized liquid spray;

at least one delivery tube for delivering pressurized gas to said spray nozzle; and a pump for said liquid, wherein said pump is configured to operate in pulses;

wherein said apparatus is configured in such a way that the gas stream ejected from said at least one gas outlet has a direction of motion, and the atomized liquid spray generated by said spray nozzle has the direction of motion of the gas stream.

2. The apparatus according to claim 1, further comprising a controller configured to control the gas pressure within said delivery tube in the range from 0.1 to 10 bar.

3. The apparatus according to claim 1, further comprising a controller configured to cause the liquid to be ejected from said liquid outlet with a low pressure in the range from 0.1 and 0.5 bar.

4. The apparatus according to claim 1, further comprising a controller configured such that the liquid flow through said pump is in the range from 0.001 to 10 ml/min.

5. The apparatus according to claim 1, wherein said liquid outlet has an orifice, wherein said orifice has a diameter from 0.1 to 1 mm.

6. The apparatus according to claim 1, further comprising a controller configured to operate said pump with a frequency from 0.1 to 1 kHz.

7. The apparatus according to claim 1, further comprising a controller in communication with a temperature measuring unit which measures the temperature of the tissue, and the controller is configured to regulate said pump and/or said at least one delivery tube according to the measured temperature of the tissue.

8. The apparatus according to claim 1, wherein said spray nozzle comprises one liquid outlet in combination with a plurality of gas outlets.

9. The apparatus according to claim 8, wherein each one of said plurality of gas outlets has a corresponding delivery tube, and further comprising a controller configured to control the gas flow from each gas outlet independently of the other gas outlets.

10. The apparatus according to claim 8, wherein each gas outlet of said plurality of gas outlets is aligned to a different point within the treatment area and its surroundings.

11. A laser system including a handpiece, wherein the apparatus according to claim 1 is mounted on said handpiece.

12. The laser system according to claim 11, wherein said apparatus is configured in such a way that the spray operation is synchronized with the laser pulses of the laser system.

13. The laser system according to claim 11, wherein a device which ejects a jet of cold air is additionally mounted on said handpiece.

14. The laser system according to claim 11, further comprising a spacer with a fixed length for keeping the height of the spray nozzle above the treatment area approximately constant, wherein the spacer is configured to contact a region of the tissue surface outside the treatment area.

* * * * *